(12) United States Patent
Gonzalez Garcia et al.

(10) Patent No.: US 11,786,579 B2
(45) Date of Patent: Oct. 17, 2023

(54) INJECTABLE PRESENTATIONS, SYRINGES AND COMPOSITIONS WITH SUSTAINED AND/OR CONTROLLED RELEASE OF LANREOTIDE

(71) Applicant: EDIX SA, Luxembourg (LU)

(72) Inventors: Maria Isabel Gonzalez Garcia, Cubelles (ES); José Maria Roca Torrellas, Barcelone (ES); Tabatha Bourgois, Barcelone (ES); Laurence Lachamp, Gava Barcelone (ES); Frederic Lacombe, Sant Cugat Del Valles (ES)

(73) Assignee: EDIX SA, Luxembourg (LU)

( * ) Notice: Subject to any disclaimer, the term of this patent is extended or adjusted under 35 U.S.C. 154(b) by 0 days.

(21) Appl. No.: 17/042,617

(22) PCT Filed: Mar. 28, 2019

(86) PCT No.: PCT/EP2019/057845
§ 371 (c)(1),
(2) Date: Sep. 28, 2020

(87) PCT Pub. No.: WO2019/185786
PCT Pub. Date: Oct. 3, 2019

(65) Prior Publication Data
US 2021/0023178 A1    Jan. 28, 2021

(30) Foreign Application Priority Data
Mar. 28, 2018 (FR) ...................... 18/52662

(51) Int. Cl.
A61K 38/00    (2006.01)
A61K 38/25    (2006.01)
A61P 5/08    (2006.01)
A61M 5/315    (2006.01)
A61M 5/178    (2006.01)
A61M 5/31    (2006.01)

(52) U.S. Cl.
CPC ............ *A61K 38/25* (2013.01); *A61M 5/178* (2013.01); *A61M 5/315* (2013.01); *A61M 5/31511* (2013.01); *A61M 5/31513* (2013.01); *A61M 5/31596* (2013.01); *A61P 5/08* (2018.01); *A61M 2005/3128* (2013.01)

(58) Field of Classification Search
CPC ........ A61K 38/25; A61K 38/08; A61K 47/10; A61K 47/183; A61K 9/0019; A61K 9/10; A61M 5/31596; A61P 5/08; A61P 27/02; A61P 35/00
See application file for complete search history.

(56) References Cited

U.S. PATENT DOCUMENTS

| | | | |
|---|---|---|---|
| 2011/0124563 A1* | 5/2011 | Parente Duena | .... A61K 9/1647 514/11.1 |
| 2012/0156259 A1 | 6/2012 | Rau et al. | |
| 2015/0374929 A1* | 12/2015 | Hyde | ................... A61K 9/1647 |

FOREIGN PATENT DOCUMENTS

| | | | |
|---|---|---|---|
| EP | 2823808 A1 * | 1/2015 | ............. A61K 38/08 |
| WO | 96/07398 | 3/1996 | |
| WO | 2011/085957 | 7/2011 | |
| WO | WO-2011085957 A2 * | 7/2011 | ............. A61K 38/04 |
| WO | 2015/004125 | 1/2015 | |
| WO | 2016/022831 | 2/2016 | |

OTHER PUBLICATIONS

Liang et al. Food and Chemical Toxicology 115 (2018) 315-328. L-Arginine induces antioxidant response to prevent oxidative stress via stimulation of glutathione synthesis and activation of Nrf2 pathway (Year: 2018).*
Search Report for FR Application No. 1852662 dated Nov. 20, 2018, 4 pages.
International Search Report for PCT/EP2019/057845 dated Jun. 11, 2019, 8 pages.
Written Opinion of the ISA for PCT/EP2019/057845 dated Jun. 11, 2019, 8 pages.

* cited by examiner

*Primary Examiner* — Aradhana Sasan
*Assistant Examiner* — Mercy H Sabila
(74) *Attorney, Agent, or Firm* — NIXON & VANDERHYE

(57) ABSTRACT

The present invention relates to novel injectable presentations, kits or syringes comprising a composition with sustained or controlled release of lanreotide or one of the salts thereof. The compositions of lanreotide or one of the salts thereof are packaged in a syringe having a diameter greater than 3.00 mm and provided with a needle having an outer diameter no greater than 1.00 mm.

16 Claims, 5 Drawing Sheets

INJECTABLE PRESENTATIONS, SYRINGES AND COMPOSITIONS WITH SUSTAINED AND/OR CONTROLLED RELEASE OF LANREOTIDE

This application is the U.S. national phase of International Application No. PCT/EP2019/057845 filed Mar. 28, 2019 which designated the U.S. and claims priority to FR Patent Application No. 1852662 filed Mar. 28, 2018, the entire contents of each of which are hereby incorporated by reference.

The present invention relates to new injectable presentations for pharmaceutical compositions intended for the sustained and/or controlled release of lanreotide.

More particularly, the subject of the present invention is new injectable presentations, kits or syringes comprising a composition with sustained or controlled release of lanreotide or of one of its salts.

The marketed lanreotide often used in acetate form is an octapeptide analog of natural somatostatin. Like somatostatin, lanreotide is an inhibitor of various endocrine, neuroendocrine, exocrine and paracrine functions. It exhibits high affinity for human somatostatin receptors (SSTR) 2 and 5, and low affinity for SSTR 1, 3 and 4. The main reason for inhibition of growth hormone is this activity at the SSTR 2 and 5 receptors. Lanreotide is more active than natural somatostatin and has a longer period of action. Its marked selectivity for growth hormone secretion compared with that of insulin first made it a product with suitable compositions for the treatment of acromegaly.

Today, the main field of application of lanreotide is the treatment of neuroendocrine tumors (NET), first the symptoms of carcinoid syndromes then the control of these tumors thanks to its antiproliferative activity, the compositions developed to treat acromegaly have been used so far. These compositions allow low doses to be delivered continuously for years.

Regarding the treatment of neuroendocrine tumors, it is important to be able to quickly adapt each treatment to each evolution of the disease, but also to be able to easily administer higher doses, the benefits of which are known for the treatment of carcinoid syndromes because this allows to better control the evolution of these tumors over longer periods. This would be easier with products which immediately give the necessary levels and whose release can be interrupted more quickly, whether the period of administration is several weeks or several months. It would also be desirable for this aim to be obtained with products that are easier and more comfortable to inject.

Compositions of lanreotide are described in patent application WO9607398 which mentions solid or semi-solid forms of gellable peptides including lanreotide, which will gel to give a prolonged release of lanreotide. Mention is also made of suspensions or semi-solid compositions, described as highly viscous or pasty, in which a solvent is added to obtain the semi-solid consistency which automatically forms a gel after interaction with body fluids. The controlled release of the composition of lanreotide is described as highly dependent on the viscosity and the volume of the product injected. These semi-solids are also described as extrusion rods or "bars", in relation to the importance given to preserving the shape of the injected product and the specified obligation to inject the product with a large diameter needle. The amount of solvent (water) is specified as having to be limited so as to avoid any risk of solubilization of the gellable lanreotide, in order to preserve a resistant deposit, which will gel at the injection site.

Document WO 9607398 also explains the importance given to the shape and volume of the deposit. It is shown that by reducing the diameter of the deposit of lanreotide during injection, a much more variable control of the release in vitro is observed. Overly diluted compositions are considered undesirable because they disperse after injection and do not form the gel responsible for the sustained release of the product.

Document WO2015004125 describes a pharmaceutical composition for a prolonged period of action of at least two months, comprising lanreotide as active ingredient at a concentration ranging from 35 to 55% by weight relative to the total weight of the composition, a co-solvent chosen from low molecular weight water soluble polymers such as polyvinylpyrrolidone (PVP) and polyethylene glycol (PEG), N-methyl-2-pyrrolidone (NMP), N-ethyl-2-pyrrolidone (NEP), propylene glycol, glycerol, glycofurol, ethanol, benzyl alcohol and a mixture of these, and water.

Lanreotide is marketed and used in products such as Somatuline®, Autogel®, Somatuline L.P. or Somatuline® Depot. The product Somatuline L.P. 120 mg, for example, is in the form of a specific pre-filled syringe of 0.5 mL comprising an automatic safety system and a specific pre-assembled needle of 1.20 mm×20 mm. The marketed compositions contain lanreotide acetate which is in the form of a pasty product of whitish and translucent appearance which must be injected into the upper-outer quadrant of the buttocks, by pushing the needle in its entire length (deep subcutaneous route). Subsequently and for the sake of simplification, by "Somatuline®" shall be understood without limitation "Somatuline®, Autogel®", "Somatuline LP", "Somatuline® Depot" or any other trade name given to the product.

The marketed compositions have been formulated to obtain, after injection of lanreotide acetate, a form and a deposit volume leading to in-situ gelation in contact with bodily fluids. To achieve this effect, it is necessary to use needles with an inner diameter of at least 1.00 mm to obtain a compact deposit. This type of needle allows the injection of semi-solid, pasty or very viscous products.

The commercial compositions existing to date contain a lanreotide concentration of 25% by weight. In order to be able to inject this pasty product, it is necessary to use a special syringe with a small inner diameter of approximately 3.00 mm and a length of 80 mm. The product injected can only be of a maximum volume of 0.5 mL. However, the thinness and the length of the syringe pose problems for implanting a large needle and comfortably and precisely injecting this very viscous product.

Moreover, it can be noted that needles with an inner diameter of at least 1 mm are also responsible for pain problems at the injection site or as a result of the formation of nodules. Another constraint, related to the pasty consistency of lanreotide, encountered with a 25% by weight lanreotide composition is the inability to inject the product intramuscularly because of the excessive injection force associated with the pressure loss with a needle at least 25 mm in length. It is also not desirable to inject the lanreotide of such a composition by the superficial subcutaneous route because of the excessive diameter of the needle and the low local tolerance of a deposit which is not very deformable.

The marketed compositions based on lanreotide are used for deep subcutaneous administration, over periods which may vary from weeks to once a month or once every 2 months in certain patients, for treatments which may extend over several years.

With the current 20 mm long needles, this deep subcutaneous route can sometimes be intramuscular or at the border of the two tissues. It would therefore be useful to have an injectable presentation and a composition which makes it possible to choose the injection route with greater precision. In certain cases, it may also be desirable to prefer the intramuscular route, for example to avoid possible risks of local tolerance or of an immune response linked to the active compound.

There is therefore a great need to simplify the injections, to make them less painful and to be able to change the type and the location of the deposits in order to avoid the problems of nodules. There is also a need to improve the lanreotide release profiles to cover the needs at the end of the interval before reinjection in the case of acromegaly, or to increase the levels and better control the release profiles in the case of neuroendocrine tumors. It is clear that there is an unmet medical need to which it is desirable to provide answers by proposing new compositions whose administration can be based on simple or even standard devices, of the syringe type provided with a manually actuated piston.

Since the start of the development of the sustained-release compositions of lanreotide currently on the market, the composition chosen to meet the needs for higher doses of lanreotide has consisted of bringing the injections closer in time or increasing them at the same time but without satisfactorily solving the problems related to these injections.

Indeed, the use of a manual device of the standard syringe type with a thinner needle combined with a less viscous composition of lanreotide has never been envisaged because this composition was going against an unfavorable prejudice for the one skilled in the art.

In fact, those skilled in the field of pharmaceutical compositions know that a decrease in the lanreotide concentration, even by a few percent, will have the effect of reducing the viscosity and therefore a faster solubilization of the lanreotide composition in contact with bodily fluids at the injection site.

In view of the teaching of the prior art and in particular of application WO 9607398, it is possible to expect that the delayed effect caused by the gelation of the concentrated product no longer occurs, resulting in rapid release of the product.

Furthermore, application WO 9607398 also recommends the use of a needle with an inner diameter of at least 1.00 mm in order to inject the lanreotide so that the deposit of the product maintains a release profile of at least 15 days.

The administration of a composition of lanreotide having a lower concentration than that described in this application with a needle of less than 1.00 mm therefore goes against the teaching of the prior art on two essential points which are the characteristics of the present invention.

Quite unexpectedly, the authors of the present invention carried out research and demonstrated the fact that a less viscous composition of lanreotide could lead to deposits which are different from the gels previously described but which are also capable of giving a controlled release of lanreotide, when said composition is injected using a thinner needle than that used for commercial compositions. This discovery makes it possible to produce lanreotide compositions which reduce or eliminate the disadvantages associated with the specific manufacture and the complex use of the compositions currently marketed.

The improvements and simplifications brought to the injections by this invention may thus allow pre-filled presentations of sustained and/or controlled release compositions of lanreotide in the conventional reservoirs of standard injection devices such as syringes or the usual glass or polymeric cartridges (ex. Cyclo Olefin Polymers or COC cyclic olefin copolymer). These improvements are such that they allow the use of reservoirs of conventional sizes and diameters of these pre-filled presentations which were not compatible with the needs of prolonged and/or controlled injection and the current compositions whose commercial presentations require specific techniques for filling in small diameter reservoirs combined with large diameter needles, or particular injection devices which make it possible to carry out injections of deposits with prolonged or controlled release.

DESCRIPTION OF THE INVENTION

Thus, the present invention consists in providing new injectable compositions based on lanreotide or one of its derivatives, such as its salts, allowing:

to reduce injection problems such as the implantation difficulties of the needles with an inner diameter of at least 1.00 mm, to reduce undesirable effects at the injection site such as the appearance of nodules, to enrich the range of treatment by offering for example intramuscular, intradermal, intraocular or superficial subcutaneous administrations.

More particularly, the present invention relates to a novel injectable presentation of a pharmaceutical composition comprising:

a) an aqueous solvent consisting of water and optionally of an organic solvent miscible with water, preferably an alcohol, even more preferably ethanol, b) lanreotide or one of its salts at a concentration ranging from 11 to 25% by weight of lanreotide, preferably from 18 to 25%, more preferably from 18 to 22%, even more preferably from 18 to 21% in weight of lanreotide relative to the total weight of the composition, c) optionally one or more amino acids, preferably arginine, d) optionally a monomeric excipient accepted by the pharmacopoeia, these new compositions being packaged in a syringe with a diameter greater than 3.00 mm, preferably greater than or equal 3.50 mm in diameter, more preferably greater than 4.00 mm up to 7.00 mm in diameter provided with a needle with an outer diameter equal to or less than 1.00 mm, an inner diameter equal to or less to 0.80 mm and a length preferably between 10 and 40 mm, preferably a length of 20 to 30 mm.

In particular when syringes of the HyPak™ or HyLok™ type or plastic syringes made of COP of the Clearject® type are used, the inner diameter of the syringes is more preferably greater than 4.00 mm up to 7.00 mm in diameter.

According to another aspect, the present invention therefore relates to a pre-filled syringe characterized in that:

a. its diameter is greater than 3.00 mm, preferably greater than or equal to 3.50 mm in diameter, more preferably greater than 4.00 mm up to 7.00 mm in diameter and it is equipped with a needle having a outer diameter equal to or less than 1.00 mm and an inner diameter equal to or less than 0.80 mm and a length preferably between 10 and 40 mm, preferably a length of 20 to 30 mm, b. it contains a pharmaceutical composition comprising:

1) an aqueous solvent consisting of water and optionally of an organic solvent miscible with water, preferably an alcohol, even more preferably ethanol, 2) lanreotide or one of its salts, preferably lanreotide acetate at a concentration ranging from 11 to 25% by weight of lanreotide, preferably from 18 to 25%, more preferably from 18 to 22%, even more preferably of 18 to 21% by weight of lanreotide relative to the total weight of the composition,
3) optionally one or more amino acids, preferably arginine,
4) optionally a monomeric excipient accepted by the pharmacopoeia.

According to another aspect, the present invention relates to an assembly composed of a syringe pre-filled with a pharmaceutical composition characterized in that:
a) the pre-filled syringe has a diameter greater than 3.00 mm, preferably 3.50 mm in diameter, more preferably greater than 4.00 mm up to 7.00 mm in diameter and is equipped with a needle having an outer diameter equal to or less than 1.00 mm and an inner diameter equal to or less than 0.80 mm and a length preferably between 10 and 40 mm, preferably a length of 20 to 30 mm,
b) the pharmaceutical composition comprises or consists of:
1) an aqueous solvent consisting of water and optionally of an organic solvent miscible with water, preferably an alcohol, even more preferably ethanol,
2) lanreotide or one of its salts, preferably lanreotide acetate at a concentration of 11 to 25%, preferably 18 to 25%, more preferably 18 to 22%, more preferably 18 to 21% in weight of lanreotide relative to the total weight of the composition,
3) optionally one or more amino acids, preferably arginine,
4) optionally a monomeric excipient accepted by the pharmacopoeia, said pharmaceutical composition being contained in said syringe.

According to a preferred embodiment of the invention, the monomeric excipient is at least one compound chosen from lactose, dextrose, sucrose, mannitol, sorbitol, glucose, fructose, mannose, galactose, arabinose, fucose, citric acid or one of its salts or esters, lactic acid or one of its salts or esters, acetic acid or one of its salts or esters and mixtures thereof and the pharmaceutical composition according to the present invention does not contains polymeric excipient such as (d, l) polylactic acid (PLA), a copolymer of lactic acid and glycolic acid (PLGA), polyphenylene propylene, a copolymer of ethylene and vinyl acetate; a fatty acid/sebacic acid copolymer, a poly (erucic acid dimer-sebacic acid) copolymer, a poly (fumaric acid-sebacic acid) copolymer, chitin, collagen, gelatin, monomethyl polyethylene glycol/polylactic acid, monomethyl polyethylene glycol/polylactic acid copolymers, polyethylene glycol/polylactic acid or a polyethylene glycol/polylactic acid copolymer.

According to a preferred embodiment, the present invention relates to a manual syringe with a piston rod provided with a standard needle of the luer-lock type having an outer diameter of 0.80 to 1.00 mm, an inner diameter and 0.60 to 0.80 mm and a length of about 20 mm, pre-filled with a sustained-release pharmaceutical composition for parenteral administration, said composition comprising an aqueous solvent consisting of water and optionally 3% ethyl alcohol, acetate lanreotide in an amount sufficient so that the lanreotide concentration is preferably from about 18 to 25%, more preferably from 18 to 22%, even more preferably from 18 to 21% by weight relative to the total weight of the composition, and optionally arginine at a concentration ranging from 0.1 to 13% by weight relative to the total weight of the composition.

More particularly, the invention relates to a manual syringe with a piston rod provided with a standard needle of the luer-lock type having an outer diameter of approximately 0.80 mm, an inner diameter of approximately 0.60 mm and a length of about 20 mm, pre-filled with a composition or a sustained release pharmaceutical suspension for parenteral administration, said composition comprising water and lanreotide acetate in an amount sufficient so that the concentration of lanreotide or about 20% by weight relative to water.

According to one embodiment of the invention, a kit comprises a pharmaceutical composition as described above and a syringe the needle of which has an outer diameter equal to or less than 1.00 mm, an inner diameter equal to or less than 0.08 mm and a length preferably between 10 and 40 mm.

The injection is performed by manually actuating the plunger rod along the syringe.

According to a preferred embodiment, the present invention also relates to a pre-filled syringe, said syringe containing the pharmaceutical composition as defined above for a sustained release of an active compound for at least 1 month.

According to another embodiment of the invention, the syringe is a standard manual syringe of the luer-lock type with a standard piston rod provided with a needle which may be standard, said needle having an outer diameter of 0.90 to 1.00 mm, an inner diameter of 0.70 to 0.80 mm and a length of 20 to 30 mm.

According to another preferred embodiment of the invention, the standard manual syringe of the luer-lock type comprising a standard piston rod provided with a needle which may be standard, said needle having an outer diameter of 0.90 mm, an inner diameter of 0.70 mm and a length of 20 mm, pre-filled with a pharmaceutical composition with sustained release for parenteral administration, said composition comprising an aqueous solvent consisting of water and ethyl alcohol at 3% by weight relative to the total weight of the composition of lanreotide with a concentration of preferably 18 to 25%, more preferably 18 to 22%, more preferably 18 to 21% by weight relative to the total weight of the composition and of the arginine of 0.1 to 13% by weight relative to the total weight of the composition.

According to another preferred embodiment of the invention, the manual syringe comprises a plunger rod provided with a standard needle of the luer-lock type having an outer diameter of approximately 0.80 mm, an inner diameter of approximately 0.60 mm and a length of about 20 mm, pre-filled with a sustained release pharmaceutical composition for parenteral administration, said composition comprising water and lanreotide acetate at a concentration of 20% lanreotide by weight relative to the total weight of the composition.

According to a preferred embodiment, the present composition is administered parenterally by normal or deep subcutaneous injection, or intramuscularly into a patient.

According to a preferred embodiment, the present composition is such that parenteral administration by normal or deep subcutaneous injection, or intramuscularly into a patient of said composition using said syringe, releases lanreotide or the salt of lanreotide over a period of at least 7 days, 7 to 14 days, 14 to 28 days, preferably at least 28 days.

According to a preferred embodiment, the present composition is in a form suitable for parenteral administration by subcutaneous, normal or deep injection, or intramuscular injection into a patient of said composition using said syringe releasing lanreotide or the salt of lanreotide over a period of at least 7 days, 7 to 14 days, 14 to 28 days, preferably at least 28 days.

According to a preferred embodiment, the lanreotide is in the form of a salt or of a free base.

The salts of lanreotide which can be used for the invention are preferably pharmaceutically acceptable salts of organic acids, such as those of acetic, phenylacetic, lactic, malic, pamoic, ascorbic, succinic, benzoic, methanesulphonic or toluenesulphonic acids, or pharmaceutically acceptable salts, acceptable inorganic acids such as hydrochloric, hydrobromic, hydriodic, sulfuric or phosphoric acids.

According to a preferred embodiment, the lanreotide is in the form of lanreotide acetate.

According to another preferred embodiment, the lanreotide is in the form of a free base.

Whatever the form of lanreotide, that is to say in saline or free base form, within the meaning of the present invention, the amount of lanreotide, expressed for example as a concentration or as a percentage in the composition, denotes lanreotide under free base form.

Advantageously, lanreotide is present at a concentration of 18%, 18.5%, 19%, 19.5%, 20%, 20, 5%, 21%, 21.5%, 22%, 22.5%, 23%, 23.5%, 24%, 24.5%, or 25% by weight relative to the total weight of the composition.

If one defines as injectable semi-solid a composition which after injection forms a easy to manipulate, solid extrudate, the pharmaceutical composition as such or present in a pre-filled syringe according to the present invention is a viscous composition, but not semi-solid. This composition can be injected using a standard injection device such as a syringe with a manually operated plunger rod fitted with a conventional needle. Preferred sizes of syringe and needle are shown above.

The viscosity and other physical state characteristics of the compositions can be evaluated as injectability, when the administration step is evaluated. Injectability can be determined by performing mock injection tests and by different physical methods. Injectability can be reported as injection strength or syringe injection strength (SIF).

The term "injectability" which can be determined by measuring the force of injection, refers to the suitability of the composition for parenteral administration using an injection device, such as a syringe or injector. SIF can be determined using a dynamometer (L1000R, Lloyd Instruments Ltd.) fitted with a calibrated cell (NLC 100N, Lloyd Instruments Ltd.). The pharmaceutical composition according to the present invention can be packaged in a syringe the diameter of which is greater than 3.00 mm, preferably greater than or equal to 3.50 mm in diameter, more preferably greater than 4.00 mm up to 7.00 mm in diameter coupled to a 20 mm long needle for an inner diameter varying from 0.60 to 1.00 mm comparable to current needles and tested for its suitability for injection during a simulated discharge at a slow speed of 100 mm/min, where the force applied by the instrument on the piston and its displacement are recorded.

The simulated injection is performed vertically in air. The maximum injection force expressed in Newtons (N) is derived from data collected during discharge. Such examples of injection forces are detailed in Example 9.

It is known to those skilled in the art that with such finer needles it is not possible to perform manual injections of commercial products of the Somatuline® type, even with finer syringes of the Somatuline® type, and therefore even less with standard syringes with a larger inner diameter.

According to a preferred embodiment, the pharmaceutical composition as such or present in a pre-filled syringe according to the present invention has an injectability defined by a SIF ranging from 5, 6, 7, 8, 9, 10, 11, 12, 13 or 14 N when tested with the method defined above.

According to a preferred embodiment, the pharmaceutical composition as such or present in a pre-filled syringe according to the present invention exhibits an injectability defined by an SIF ranging from 5 to 12 N or from 5 to 14 N when it is tested with the method defined above and a needle with an inner diameter of 1.00 mm for a composition containing preferably from 18 to 25%, more preferably from 18 to 22%, even more preferably from 18 to 21% of lanreotide.

Preferably, the SIF of the pharmaceutical composition as such or present in a pre-filled syringe according to the present invention ranges from 5 to 6 N.

According to another preferred embodiment, the pharmaceutical composition as such or present in a pre-filled syringe according to the present invention has an injectability defined by a SIF ranging from 7 to 12 N or from 5 to 14 N when it is tested with the method defined above and a needle with an inner diameter of 0.80 mm for a composition containing preferably from 18 to 25%, more preferably from 18 to 22%, even more preferably from 18 to 21% of lanreotide, always less than the SIF of the 25% commercial product of lanreotide. Preferably, the SIF of the pharmaceutical composition as such or present in a pre-filled syringe according to the present invention ranges from 7 to 9 N.

According to a preferred embodiment, the pharmaceutical composition as such or present in a pre-filled syringe according to the present invention has an injectability defined by a SIF ranging from 9 to 14 N when it is tested with the method defined above and a needle with an inner diameter of 0.6 mm for a composition preferably containing from 18 to 25%, more preferably from 18 to 22%, even more preferably from 18 to 21% of lanreotide.

Preferably, the SIF of the pharmaceutical composition as such or present in a pre-filled syringe according to the present invention ranges from 9 to 12 N.

By comparison, a commercial composition of 25% lanreotide cannot be manually extruded from a device comprising a syringe having a diameter greater than 3.50 mm. To inject such a composition, it would be necessary to use a syringe 3.50 mm in diameter, coupled to a needle 20 mm in length and 1.00 mm in inner diameter and apply a force greater than 14N, with a very slowly injection.

The injection force measured in newtons with a device different from the commercial device under the same conditions in all cases, goes for example from 14.3N with a "24.6% composition" representative of the commercial Somatuline® form to 5.5N for a composition of 19% lanreotide in water.

Knowing that there is a residual force in the order of 2N linked to the friction of the device during vacuum injection, this is a reduction of more than 70% of the force required for the injection of these 2 compositions, however close, which demonstrates a useful threshold of exploitable property according to the invention. Unexpectedly, a relatively small decrease in concentration results in a very large decrease in injection force.

In terms of implantation force, the decrease in the diameter of the needle leads to a reduction which can make a decisive difference between a needle which can be easily implanted, including by the patient himself, and a complicated implantation procedure which requires the experience, technique and practice of a specialist.

The implantation forces of the needles are proportional to the calibres or gauges of said needles. An apparently small difference in diameter such as between 1.00 mm and 1.20 mm corresponds to an impact surface or section 1.5 times larger.

The importance of reducing the diameter of the injection needle as much as possible to avoid pain and facilitate injection is illustrated in the article "Fracture mechanics model of needle cutting tissue" by Barnett et al. (2015), in which the authors demonstrate that there is a threshold for the force of penetration or insertion of needles through the skin:

For needles with an outer diameter ranging from 1.60 mm (16 G) to 1.20 mm (18 G), the forces are comparable and vary between 2.5 and 3 N, which could be considered high by those skilled in the art;

For needles with an outer diameter ranging from 0.80 mm (21 G) to 0.50 mm (25 G), the forces are reduced by two, and vary between 1 and 1.5 N.

In fact, these apparently small differences in diameter correspond to a pressure drop and therefore to an increase in the injection force which for the same product can make manual administration impossible.

Another limitation of the needles used in current commercial presentations such as Somatuline® is also linked to the need to use fine-walled cannulas of, for example 0.10 mm, so as not to increase the outer diameter. This reduces the possibilities of having a long bevel and worked to be sharp and thus increases the risks of deformation and coring during implantation. All of this may require unusual and complicated techniques, such as pulling on the skin before the needle is implanted. All of these effects are likely to complicate and make it more painful to insert the needle into the tissues. One of the advantages of the invention is therefore also to be able to return to cannulas with thicker walls, for example ranging from 0.10 to 0.20 mm, preferably 0.15 mm.

Indeed, the bevel of a needle determines how the incision will be made and how it will allow the penetration of the cannula to inject the product. On a needle of more than 1.00 mm outer diameter, it is more interesting to have thick walls to have more freedom on the design of its bevel: in fact, with thin walls it is difficult to freely shape the tip of the needle, which can make the incision complicated and therefore painful for the patient.

By using standard needles (1.00 mm and less in outer diameter) according to the invention, it is possible to modify the bevel to order, and therefore to improve the comfort of the user for a needle of outer diameter which remains lower than that of the needles of current commercial compositions.

Finally, a needle of 1.00 mm and less in outer diameter implies less penetrating force and can therefore have a bevel made on a wall thickness of only 0.10 mm, thus reducing its outer diameter compared to the inner diameter.

Conversely, a needle of 1.20 mm and more in outer diameter implies more penetrating force and would rather require a bevel made to a thickness of 0.15 mm, further increasing its outer diameter compared to the inner diameter.

A composition of up to 21% or 22% or even 25% of lanreotide can be conventionally loaded before placing the plunger, for example of butyl in a BD Hypak™ Long of 1 mL syringe stoppered with a luer-lock stopper, or a 0.5 mL plastic syringe in COP of the Clearject® type (Gerresheimer). It is possible to perform injections by fixing to the luer-lock end a standard 21 G needle of 25 mm or 16 mm to obtain the same profiles at different injection conditions and depths, this also thanks to the deposit conditions.

According to another subject of the invention, the pharmaceutical composition as such or present in a pre-filled syringe further comprises an alcohol, preferably ethanol. Those skilled in the art might have thought that adding organic solvents even in low concentrations of about 5 to 10% by weight in water would have led to stability problems.

The inventors have discovered that it is possible in presentations according to the invention to use this type of mixture with ethanol at a concentration of at least 5% and up to 25% in water which makes it possible to obtain stable and homogeneous lanreotide compositions.

With low percentages of alcohol which do not pose a problem of pain on injection or of local tolerance, the inventors have unexpectedly discovered that these compositions are more viscous than those obtained with water alone at the same concentration of lanreotide, possibly explaining the stability of the active substance under these conditions.

The pharmaceutical compositions as such or present in a pre-filled syringe according to the present invention comprising from 3 to 23% and preferentially from 3 to 10% of ethanol, on the other hand, make it possible to use and more easily validate methods for ready to use aseptic preparations, without resorting to gamma-irradiation in terminal sterilization. They also make it possible to envisage solid presentations of lanreotide which is stable at room temperature with simple and rapid extemporaneous preparations of the product to be injected.

According to another preferred embodiment, the pharmaceutical composition as such or present in a pre-filled syringe according to the present invention comprises ethanol at a concentration of 3 to 23% by weight relative to the total weight of the composition, preferably from 3 to 10% by weight relative to the total weight of the composition.

According to another preferred embodiment, the pharmaceutical composition as such or present in a pre-filled syringe according to the present invention containing lanreotide at 20% by weight, ethanol at a concentration of 5 to 25% by weight in water has an injectability defined by a SIF ranging from 7 to 9 N when tested with the method defined above.

Preferably, the SIF of the pharmaceutical composition ranges from 7 to 8 N. For example, the injection strength test carried out with pharmaceutical compositions containing lanreotide at 20% by weight, and 5% or 10% ethanol in water, shows forces of 8.3 N and 7.3 N respectively.

These forces are almost 50% lower than that of a representative mixture of the 25% commercial product. If we consider that a hand injection force around 15 N represents an acceptable maximum under the test conditions, any reduction in force proposed by a presentation according to the invention which deviates sufficiently from this maximum constitutes a significant improvement.

With these new compositions based on a water-ethanol mixture, it is also possible to prepare higher concentrations of lanreotide, for example close to 25%, comparable to commercial products, and to use a greater proportion of ethanol but still in a small amount to be injectable without problem, for example less than or equal to 25% in water. A much more fluid composition than the current products is then obtained (see Example 9). According to the injection force test, such a composition can be injected for example with a needle of 0.80 mm inner diameter with a force of 7.3 N, i.e. 70% less than that of a mixture representative of the commercial product at 25% of lanreotide.

A subject of the invention is therefore also a pharmaceutical composition as such or present in a pre-filled syringe according to the present invention containing lanreotide at a concentration of approximately 18% to 25% and ethanol at a concentration of 3 to 23% by weight, these percentages being expressed relative to the total weight of the composition.

The results obtained on animals and presented in the examples indicate that the water-ethanol compositions of the present invention, compared to the commercial forms, make it possible to envisage new profiles for the release of lanreotide, and therefore also make it possible, for example, to reduce the burst or Cmax by 1.5 to 2 times compared to the commercial product, which also makes it possible to multiply by at least 2 the circulating levels of lanreotide 2 to 4 weeks after the injection. (See FIGS. 2-4)

Preferably the compositions, kits or pre-filled syringes according to the invention which do not comprise ethanol comprise from 18 to 25%, more preferably from 18 to 22%, even more preferably from 18 to 21% by weight of lanreotide per relative to the total weight of the composition, and those comprising ethanol comprise from 18 to 25% of lanreotide by weight of lanreotide relative to the total weight of the composition.

According to another embodiment, the compositions of the invention comprise at least one amino acid, preferably arginine, present at a concentration ranging from 0.1 to 13% by weight relative to the total weight of the composition.

We have also demonstrated that depending on the proportions and mixing conditions (type of medium, temperature and time) of lanreotide with at least one amino acid, it is possible to obtain a release profile of lanreotide that is better controlled than that of the current products such as Somatuline®, and a period of action of one week to several months.

This approach with the addition of an amino acid can lead to various new compositions. For example, arginine can be added to compositions comprising different concentrations of lanreotide, for example at a concentration equal to or less than 21% or 22% or else 25% in water.

The amount by weight of arginine may vary between 0.1 and 13% relative to the total weight of the composition.

According to another preferred embodiment, the pharmaceutical composition as such or present in a pre-filled syringe according to the present invention is intended for a sustained release of lanreotide for at least 1 month and comprises or consists essentially of:
18%, 18.5%, 19%, 19.5%, 20%, 20, 5%, 21%, 21.5%, 22%, 22.5%, 23%, 23.5%, 24%, 24.5% or 25% by weight of lanreotide;
from 0 to 23% by weight of ethanol, preferably from 3% to 10% by weight;
from 0 to 13% by weight of arginine, preferably 1% to 13% by weight, even more preferably 2% to 13% by weight.

It is also possible to adapt the release profile as needed, starting from the same composition, by choosing the subcutaneous (SC) or intramuscular (IM) administration route. All of these advantageous and novel features also constitute other subjects of the invention.

All these diluted forms associated with finer needles do not give controlled volume deposits for in situ gelation but lead to greater diffusions or distributions at the injection point or even to deposits of a more flattened shape, following a in-situ precipitation of lanreotide.

One would have expected under these conditions to obtain rapid or uncontrolled releases, for example by solubilization of lanreotide, but unexpectedly, this increase in the exchange surface leads to the formation of a precipitate of smaller volume which differently controls the release and this in a useful and reproducible way to solve the various problems described above with more conventional injections.

A pharmaceutical composition as such or present in a pre-filled syringe according to the present invention is administered parenterally. According to a preferred embodiment, the pharmaceutical composition as such or present in a pre-filled syringe according to the present invention is administered by subcutaneous, intramuscular or deep subcutaneous injection, and more preferably by subcutaneous injection, or by intramuscular injection.

As a new composition, the inventors have discovered, among other things, the possibility of a more diluted composition at 21% or 22% or even 25% of lanreotide at most which, injected subcutaneously, will make it possible to obtain flatter levels with a final level or Cmin higher than the current forms, either in injections every 2 or every 4 weeks. This type of profile is useful for example in acromegaly and is also likely to solve problems of lower efficiency at the end of the intervals between each injection. The same form injected intramuscularly will make it possible to obtain higher levels and Cmin than the current forms, with a profile that allows the needs to be adapted to each patient according to a time between injections specific to each case, even for a period of less than 2 weeks for the needs of higher doses as is useful for example in NET (Neuroendocrine tumors).

These new presentations are also very advantageous for locoregional applications of lanreotide such as in ophthalmology, diabetology or dermatology.

All these new presentations are easier to inject and certainly less painful than the current products, both by injection with a thinner needle and by the deposit that is less compact or resistant, and therefore more flat. They are therefore compatible even with closer injections. As indicated above, we know that the injection force can then be, for example, more than three times lower than with commercial products, which favors, or even makes possible, administration by the patient himself or by his entourage with a standard syringe-type manual device.

A pharmaceutical composition as such or present in a pre-filled syringe according to the present invention is administered parenterally.

According to a preferred embodiment, the pharmaceutical composition as such or present in a pre-filled syringe according to the present invention is administered by subcutaneous, intramuscular or deep subcutaneous injection, and more preferably by subcutaneous injection or intramuscular. For the subcutaneous route which remains preferred, the injection volume is preferably not greater than 2 or 1.9 or 1.8 or 1.7 or 1.6 or 1.5 or 1.4 or 1, 3 or 1.2 or 1.1 or 1 mL of a composition of lanreotide at a concentration ranging from 18 to 25%, more preferably from 18 to 22%, even more preferably from 18 to 21% by weight of lanreotide relative to the total weight of the composition. According to a preferred embodiment, the sustained release of lanreotide is at least 2 months in humans.

According to a preferred embodiment, the sustained release of lanreotide is at least 3 months in humans.

The pharmaceutical composition as such or present in a pre-filled syringe according to the present invention allows a sustained release for at least 7 days, 7 to 14 days, 14 to 28 days, 2 months or 60 days or more than 2 months or 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 days.

According to a preferred embodiment, the pharmaceutical composition as such or present in a pre-filled syringe according to the present invention allows a sustained release for at least 60 days.

According to another preferred embodiment, the pharmaceutical composition as such or present in a pre-filled syringe according to the present invention allows a sustained release for at least 7 days.

According to another preferred embodiment, the pharmaceutical composition as such or present in a pre-filled syringe according to the present invention allows a sustained release for at least 90 days.

According to a more preferred embodiment, the pharmaceutical composition as such or present in a pre-filled syringe according to the present invention allows a sustained release for at least 14 days.

According to another more preferred embodiment, the pharmaceutical composition as such or present in a pre-filled syringe according to the present invention allows sustained release for at least 28 days.

As previously indicated, lanreotide is a marketed analogue of somatostatin. It is indicated for the treatment of acromegaly caused by pituitary and non-pituitary growth hormone-secreting tumors, for the management of symptoms and antiproliferative treatment of neuroendocrine tumors, particularly carcinoid tumors and VIPomas, and for treatment of thyrotrophic adenoma.

A pharmaceutical composition as such or present in a pre-filled syringe according to the present invention may therefore be useful in the treatment of acromegaly due to pituitary and non-pituitary tumors secreting growth hormone, in the management of the symptoms caused. by neuroendocrine tumors as well as its control, in particular carcinoid tumors and VIPomas or for the treatment of thyrotropic adenoma. According to a preferred embodiment, a pharmaceutical composition as such or present in a pre-filled syringe according to the present invention is useful in the treatment of acromegaly or neuroendocrine tumors, for example, functional and non-functional gastroenteropancreatic neuroendocrine tumors.

According to the modalities of the invention, a patient suffering from acromegaly or NETs can be treated by administering a therapeutically active amount of the pharmaceutical composition described in any of the embodiments described below.

According to one embodiment, the pharmaceutical composition as such or present in a pre-filled syringe according to the present invention is administered or injected, or prepared for administration or injection into a patient in need thereof, no more frequently than every 2 weeks or preferably every 4 or 8 or 12 or 16 weeks. Preferably, it is administered or injected every 4 weeks.

According to another preferred embodiment, the pharmaceutical composition as such or present in a pre-filled syringe according to the present invention is administered or prepared for administration in a single injection.

Preferably, the method comprises administering the pharmaceutical composition as such or present in a pre-filled syringe according to the present invention at least once every 2 weeks or 4 weeks or 8 weeks or 12 weeks or 14 weeks or 16 weeks. More preferably, the method comprises administering the pharmaceutical composition as such or present in a pre-filled syringe according to the present invention at least once every 12 weeks.

According to another embodiment, the pharmaceutical composition as such or present in a pre-filled syringe according to the present invention is administered by single injection. Preferably, the pharmaceutical composition as such or present in a pre-filled syringe according to the present invention is injected intramuscularly, subcutaneously or deep subcutaneously.

According to another embodiment, the pharmaceutical composition as such or present in a pre-filled syringe according to the present invention is administered in a dose of 60, 90, 120 or 240 or 360 mg of lanreotide. Preferably, the pharmaceutical composition as such or present in a pre-filled syringe according to the present invention is administered at a dose of 120, 240 or 360 mg of lanreotide. The advantages of this invention which allow easier injections with finer needles and smaller less noticeable and therefore more comfortable in-situ deposits make it possible to prepare these larger doses for a single injection, such as for example double or more doses of commercial products, doses which correspond to a need for treatment, for example for neuroendocrine tumors.

According to the modalities of the invention a patient suffering from a neuroendocrine tumor can be treated by the administration of a therapeutically active amount of the pharmaceutical composition described in any of the above embodiments. Preferably, the pharmaceutical composition as such or present in a pre-filled syringe according to the present invention is administered for the antiproliferative control of neuroendocrine tumors, or to avoid the symptoms caused by these neuroendocrine tumors.

According to one embodiment, these symptoms are chosen from flushing, diarrhea and abdominal cramps.

According to the modalities of the invention a patient suffering from thyrotrophic adenoma can be treated by administering a therapeutically active amount of the pharmaceutical composition described in any of the above embodiments.

According to another embodiment, this invention allowing the formation of smaller deposits and more precision in the dosages because they are less concentrated and administered with finer needles, and thus makes it possible to prepare smaller and less viscous doses, for example for applications of lanreotide in ophthalmology, for example 20 mg or less or 0.1 mL or less, for patients with glaucoma, macular edema, inflammation, diabetic retinopathy or age-related macular degeneration. These characteristics are also suitable for applications of the product in dermatology, for example for the treatment of keloids.

The advantages of the syringes and formulations according to this invention also make it possible to carry out these injections very quickly with a short stroke of the piston for these small volumes.

According to the modalities of the invention, these less viscous formulations with a lower load of lanreotide also make it possible to produce more effectively combo-compositions in which one or more other active ingredients are added to the lanreotide which can also control their combined releases for the same treatment. For example in ophthalmology, a glucocorticoid such as dexamethasone or a monoclonal antibody or the mixture of 2 or more of these active compounds.

The pharmaceutical composition as described above is prepared by a process comprising the following steps:
preparation of the aqueous solvent comprising water and optionally ethanol and/or an amino acid, for example arginine, in a syringe
introduction of lanreotide into an appropriate container, for example in a second syringe or in a syringe-shaped container,
connection of the 2 syringes or syringe-type containers with a 2-way connector, and hydration of the lanreotide with the aqueous solvent and homogenization of the composition by means of a mixing process at a temperature between 5 and 70° C., preferably at room temperature.

In addition, the entire preparation process can be controlled with regard to critical processing parameters such as temperature, pressure, number of cycles and syringe-to-valve diameter ratio, with equipment known to the one skilled in the art.

According to another embodiment of the invention, the active ingredient can be treated beforehand alone or with arginine in an aqueous medium in proportions and for the time which vary according to the obligation to control release. Lanreotide can for example be treated by lyophilization, drying, grinding, granulation, compacting, sieving, before the preparation of the pharmaceutical composition as such or present in a pre-filled syringe according to the present invention.

Any sterilization technique such as gamma irradiation, electron beam irradiation, steam or sterile filtration for part of the process can be used to obtain a sterile pharmaceutical composition.

According to another embodiment of the invention, the preparation of the pharmaceutical composition as such or present in a pre-filled syringe according to the present invention is carried out under aseptic conditions.

A pharmaceutical composition according to the present invention may be available as a pre-filled and ready-to-use presentation. It may also be available as a ready-to-reconstitute presentation where a lyophilized product containing the active ingredient can be reconstituted extemporaneously with the aqueous solvent, and other additives as necessary as a solvent for reconstitution.

As another embodiment, the pharmaceutical composition can be packaged in pre-filled syringes.

The invention also relates to a kit comprising a pharmaceutical composition with prolonged and/or controlled release for parenteral administration, said composition comprising:
a) an aqueous solvent consisting of water and optionally of an organic solvent miscible with water, preferably an alcohol, even more preferably ethanol
b) lanreotide or a salt of lanreotide, preferably lanreotide acetate at a concentration ranging from 11 to 25% by weight, preferably from 18 to 25%, more preferably from 18 to 22%, even more preferably from 18 to 21% by weight of lanreotide relative to the total weight of the composition,
c) optionally one or more amino acids, preferably arginine,
d) optionally a pharmaceutically acceptable monomeric excipient, and a syringe whose needle has an outer diameter equal to or less than 1.00 mm, an inner diameter equal to or less at 0.80 mm and a length preferably between 10 and 40 mm.

Under the novel conditions of this invention, deposits are obtained by precipitation of lanreotide after interaction with the patient's body tissues and fluids at the injection site. This smaller and more flat type of deposit is better tolerated.

Unexpectedly, lanreotide used in more dilute forms than the semi-solid or pasty forms of current commercial compositions can be combined in a presentation with an injection device with a needle thinner than current needles of at least 1.20 mm outer diameter. The injection with this new presentation leads to a different deposit which gives controlled forms with new and advantageous properties, useful for all the therapeutic needs of the product and capable of solving the limits or problems posed by the current controlled forms.

According to another preferred embodiment, the invention relates to a pharmaceutical composition comprising:
a) an aqueous solvent consisting of water and optionally of an organic solvent miscible with water, preferably an alcohol, even more preferably ethanol,
b) lanreotide or a salt of lanreotide, preferably lanreotide acetate at a concentration ranging from 11 to 25% by weight, preferably from 18 to 25%, more preferably from 18 to 22%, even more preferably from 18 at 21% of lanreotide by weight relative to the total weight of the composition,
c) optionally one or more amino acids, preferably arginine,
d) optionally a pharmaceutically acceptable monomeric excipient, said composition being characterized in that, when it is administered by subcutaneous, normal or deep injection, or intramuscular injection into a patient using a syringe having an inner diameter in the order of 3.50 mm, more preferably greater than 4.00 mm up to 7.00 mm in diameter and is equipped with a needle having an outer diameter equal to or less than 1.00 mm and an inner diameter equal to or less than 0.80 mm and a length preferably between 10 and 40 mm, preferably a length of 20 to 30 mm, releases the lanreotide or the salt of lanreotide over a period of at least 7 days, preferably of at least less 28 days.

Animal tests were carried out in order to demonstrate that the deposits obtained, even if different, maintained the effect of controlled release or delay of lanreotide.

Depending on the objectives, it is possible to produce many different new products with the compositions of lanreotide and the kits or pre-filled syringes possible according to the invention.

Without this being limiting, the following different types of possibilities can be mentioned by way of example:
A release profile of lanreotide similar to that of current commercial forms such as Somatuline® over 4 weeks with a composition containing 20% of lanreotide in water and doses up to 120 mg in a 3.50 syringe mm in diameter fitted with a needle 0.80 mm in outer diameter and 20 mm in length for subcutaneous administration.
A higher lanreotide release profile than current forms such as Somatuline® over 4 weeks with a composition containing 20% of lanreotide in water and doses of 240 mg or more in a 3.50 mm syringe inner diameter equipped with a needle of 1.00 mm outer diameter and 20 mm in length for subcutaneous administration.
A higher lanreotide release profile than current forms such as Somatuline® over 2 weeks with a composition containing 20% of lanreotide in water and doses up to 120 mg in a 3.50 mm syringe diameter equipped with a needle 0.80 mm outer diameter and 40 mm long for intramuscular administration.
A release profile of lanreotide similar to that of current forms such as Somatuline® over 4 weeks with a composition containing 20% of lanreotide in water and doses up to 100 mg in a 3.00 mm syringe diameter fitted with a needle 0.60 mm in outer diameter and 20 mm in length for subcutaneous administration.
A release profile similar to that of current forms such as Somatuline® over 4 weeks or more with a composition containing 20% in water and doses of 20 mg or less in a syringe 3.00 mm in diameter or less equipped with a needle of 0.60 mm outside diameter or less.
A higher lanreotide release profile than current forms such as Somatuline® over 2 weeks with a composition containing 20% of lanreotide in water and doses up to 100 mg in a 3.00 mm syringe diameter equipped with a needle 0.70 mm outer diameter and 30 mm long for intramuscular administration.
A release profile of lanreotide similar to that of current forms such as Somatuline® or higher than current forms over 4 or 2 weeks with "20% compositions" in water up to more than 120 mg in a syringe standard pre-filled conventionally on which a short subcutaneous or a long intramuscular luer-lock needle of 21 or 20 G is attached.
A release profile of lanreotide similar to that of current forms such as Somatuline® or higher than the current forms over 4 or 2 weeks with a composition containing 20% of lanreotide in a 5:95 alcohol/water mixture up to more than 120 mg in a standard syringe manufactured aseptically prepared extemporaneously stable at room temperature for subcutaneous or intramuscular administration.

A lanreotide release profile that is flatter than current forms such as Somatuline® over 4 or 8 weeks with a composition containing 25% of lanreotide in a 25:75 alcohol/water mixture up to more than 120 mg in syringe standard manufactured aseptically prepared extemporaneously stable at room temperature for subcutaneous or intramuscular administration.

A lanreotide release profile that is flatter than current forms such as Somatuline® over 2, 4, 8, or 12 weeks with a composition containing 20% of lanreotide and 12% arginine in water up to more than 120 mg in a standard pre-filled syringe conventionally on which a short subcutaneous or long intramuscular luer-lock needle is attached.

DETAILED DESCRIPTION OF THE INVENTION

Figure 1:
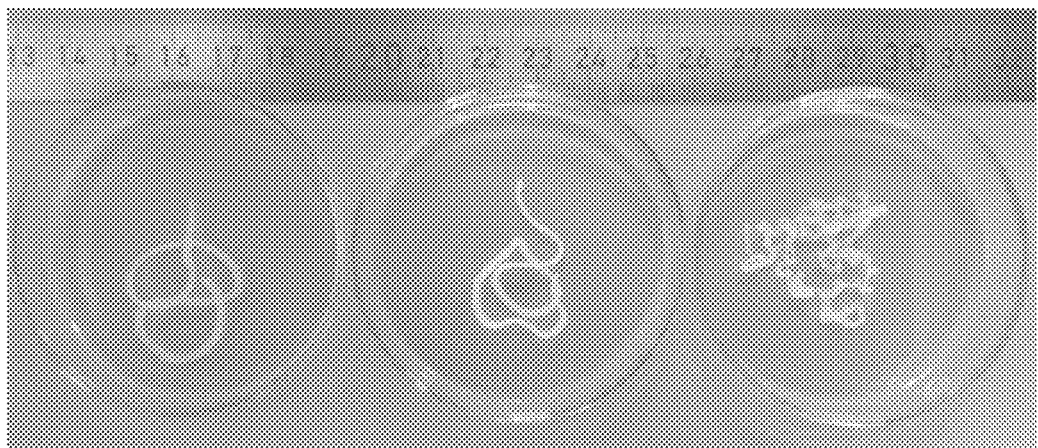
FIG. 1 shows comparable lanreotide acetate extrudates obtained after injection into air of a 19% and 25% by weight lanreotide composition contained in a 3.50 mm diameter syringe equipped with a needle of 1.00 mm inner diameter.

It is possible to describe the invention in more detail by specifying some examples of embodiments according to this invention.

EXAMPLE 1

Preparation of Compositions Between 18 and 21% or 22% or Even 25% of Lanreotide in the Form of Lanreotide Acetate in Two Types of Solvent, Water and a Water/Ethyl Alcohol Mixture 95:5%

The preparations are carried out by a back-and-forth technique between 2 syringe-type reservoirs closed on one side by a piston and open on the other by a part connected to a valve allowing optionally to condition the lanreotide acetate powder under vacuum, to hydrate this powder with solvents and to mix the product back and forth by regulating the opening of the connection by the valve, this by optionally measuring the forces exerted to control the type of mixture to be produced.

By comparing the processes for making these mixtures with those corresponding to the preparation of a composition at 25% of lanreotide comparable to the commercial product, we see that it is much easier and faster to make these preparations between 18 and 22% and that it requires less mixing force. It is also then possible to extrapolate this type of mixture to much larger volumes, or else to produce this mixture by techniques other than those specifically suited to semi-solid or pasty mixtures.

The mixing is simplified in such a way that it is also possible according to protocols known to those skilled in the art to fill syringes as is done with liquid forms, or to package the required dose in each syringe in the form of. powder or lyophilized in order to be able to hydrate it then extemporaneously and mix it manually at the time of use.

This other presentation of lanreotide according to the invention makes it possible, for example, to envisage compositions with prolonged and/or controlled release which are stable at room temperature or even compositions at variable concentrations from one and the same dose of lanreotide, in order to obtain profiles adapted to different therapeutic needs.

EXAMPLE 2

Composition Containing 19.0% of Lanreotide in Water

Batch prepared from 1.88 g of lanreotide acetate and purified water.

The preparation is carried out by the back-and-forth technique described in Example 1, using 2 plastic syringes connected to a connector which makes it possible to mix after hydration of the powder of lanreotide acetate with the water. The composition obtained is distributed in different injection systems to evaluate the injection force and other parameters such as peptide content and chromatographic purity.

EXAMPLE 3

Composition Containing 19.5% of Lanreotide in Water and Ethyl Alcohol

Batch prepared from 0.36 g of lanreotide acetate and a 95:5 mixture of purified water and ethyl alcohol. The 95:5 water-alcohol mixture is prepared by mixing 1.906 g of purified water with 0.103 g of 96% ethyl alcohol.

The preparation is carried out by the back-and-forth technique described in Example 1, using 2 plastic syringes connected to a connector which allows the mixture to be made after hydration of the lanreotide acetate powder with the water/ethyl alcohol mixture. The composition obtained is distributed in different injection systems to evaluate the injection force and other parameters such as peptide content and chromatographic purity.

EXAMPLE 4

Description of Injection Force Measurements

The injection force measurements of the compositions prepared as described in Example 1 are carried out using a dynamometer (L1000R, Lloyd Instruments Ltd.) provided with a calibrated force capture cell (NLC 100N, Lloyd Instruments Ltd.) coupled with a computer system for data acquisition and processing. For each measurement, the injection system (syringes+needles) containing the composition is placed on a support in a vertical position (needle down) and the dynamometer is used to move the plunger in the syringe to simulate an injection. The measurements are carried out at a constant displacement speed of 100 mm/min, the force detected by the cell is recorded as a function of the displacement of the piston. The composition discharged during each test can be recovered in a volumetric flask to complete the physico-chemical analyses such as, for example, the peptide content of the samples described in Example 5.

EXAMPLE 5

Description of the Process for Determining Peptide Content and Chromatographic Purity The compositions prepared as described in Examples 1, 2 and 3 are analyzed by liquid chromatography in RP-HPLC mode (standing for reverse phase high-pressure liquid chromatography). For the determination of the chromatographic purity, the area of the main peak corresponding to lanreotide is compared in % relative to the area of all the peaks detected. For the determination of the peptide content, the area of the main peak corresponding to the lanreotide is used to calculate the concentration of the composition injected, taking into account the responses (areas) obtained for the injections of compositions of lanreotide reference standards. From the concentration of the composition injected, the mass of the sample analyzed and the volume of dissolution, the peptide content (% by mass) of the composition can be calculated.

RP-HPLC conditions and method used by the inventors:
solvent for sample preparation: 0.1% acetic acid in HPLC grade water or an 85:15 mixture of acetic acid (0.1%) in HPLC grade water and acetonitrile.
column: C18 XBridge 150×4.6 mm
Column temperature: 35° C.
Mobile phase A: 0.1% trifluoroacetic acid (TFA) in HPLC quality water
Mobile phase B: 80:20 acetonitrile/water mixture of HPLC quality at 0.1% TFA
Flow rate: 0.9 mL/min
Elution: gradient of B in A (15% at 53.7% in 21.5 min then 70% at 22.5 min then 85.0% at 23.5 min)
Injection volume: between 10 and 100 µL
Concentration of the compositions: between 80 and 800 µg/mL of lanreotide
Detection: UV at 280 nm

EXAMPLE 6

Packaging of Preparations in Fine Syringes of the Commercial Insulin Type and in Conventional Pre-Fillable Syringes or Reservoirs The inventors realized that the filling of the syringes with the compositions prepared as described in Example 1 was easier to carry out, faster and less problematic than with a mixture equivalent to the 25% commercial product. The differences are so great that it is also possible here to fill syringe-type reservoirs in the traditional way as in the case of liquid injectables and to use standard reservoirs of larger diameter, such as cartridges or commercial pre-fillable syringes, glass or plastic. It is for example also possible to prepare pre-filled doses in standard glass syringes, such as, for example, of the HyPak™, HyLok™ type or in plastic COP syringes of the Clearject® type.

EXAMPLE 7

Description of the Distribution of a "19% Composition" in "Fine" Insulin-Type Syringes A batch prepared as described in Example 2 containing 19% of lanreotide in water is filled into thin plastic syringes of the insulin type of 3.50 mm inner diameter. The syringes are filled from the front by connecting the fine syringe to the end of one of the large syringes used for the preparation of the composition. The charge of the composition moves the plunger of the fine syringe backwards during its introduction.

For injected doses of 30 mg of lanreotide with a needle subsequently reported from 1.00 (OD)×0.80 (ID)×20 mm (L), 162 mg of composition is loaded into each plastic syringe. The needle is then coupled to the syringe and protected by a standard butyl stopper.

EXAMPLE 8

Description of the Distribution of a "19% Composition" in Commercial Pre-Fillable Syringes A batch prepared as in Example 2 at 19% of lanreotide in water is filled into 1.0 mL glass syringes. The glass syringes are filled from behind, as in the case of industrial filling, using a plastic cannula with an inner diameter of 3.50 mm with an outer diameter smaller than the inner diameter of the glass syringes.

For injected doses of 30 mg of lanreotide with a subsequently added 21 G needle (16 or 25 mm in length), approximately 225 mg of composition is loaded at the bottom of each glass syringe. A bromobutyl piston is then positioned to minimize as much as possible the volume of air trapped between the composition and the piston.

EXAMPLE 9

Example of Injection Force Measurements

The injection force tests are carried out according to calibrated and validated protocols, described in Example 4.

The maximum injection force expressed in Newtons (N) is derived from data collected during discharge.

In this example, representative needles of the commercial product Somatuline (1.20 mm in outer diameter and 1.00 mm in inner diameter) are compared with needles of smaller diameter, as well as the injection forces of compositions prepared according to the examples 1, 2 and 3 through the same needles and different injection systems (syringe+needle).

The results obtained are reported in the following table:

| % (w/w) lanreotide | Solvent (water:alcohol) | injection system (in mm) | Injection force (Newton) |
|---|---|---|---|
| 25.0 | 100:0 | syringe inner diameter: 3.5 needle (Dout/Din/L): 1.2/1.0/20 | 14.3 |
| 19.0 | 100:0 | syringe inner diameter: 3.5 needle (Dout/Din/L): 1.2/1.0/20 | 5.5 |
| 18.7 | 100:0 | syringe inner diameter: 3.5 needle (Dout/Din/L): 1.0/0.8/20 | 8.8 |
| 18.8 | 100:0 | syringe inner diameter: 3.5 needle (Dou/Din/L): 0.8/0.6/20 | 11.9 |

-continued

| % (w/w) lanreotide | Solvent (water:alcohol) | injection system (in mm) | Injection force (Newton) |
|---|---|---|---|
| 25 | 75:25 | syringe inner diameter: 3.5 needle (Dout/Din/L): 1.0/0.8/10 | 7.3 |
| 19.9 | 90:10 | syringe inner diameter: 3.5 needle (Dout/Din/L): 1.2/1.0/20 | 7.3 |
| 19.5 | 95:5 | syringe inner diameter: 3.5 needle (Dout/Din/L): 1.2/1.0/20 | 8.3 |

By using more dilute compositions despite the needles chosen which are much thinner and longer than those of commercial products for deep subcutaneous injections, it was observed under the conditions of the invention, reductions in injection forces by at least 3 or 4.

EXAMPLE 10

Visual Appearance and Comparisons of Extrudates Obtained by Injection Through Different Needles To demonstrate the importance of the large diameters of the needle according to known approaches before the insertion, it is possible to verify that with needles of at least 1 mm of lumen or inner diameter of commercial products at 25% of lanreotide with one of the more dilute compositions, an extruda or cylinder of the same diameter is obtained after in-vitro injection. With the finer needles combined with the more dilute compositions, the inventors have succeeded in obtaining, after in vitro injection, a product which does not keep this shape, demonstrating a capacity of this new presentation with a finer needle and a more diluted composition to not depend on the deposit to control the release of lanreotide.

Tests were conducted to evaluate the visual appearance and extrudate geometry of 2 lanreotide compositions prepared as in Example 1, through different needles.

The results are visible in FIG. 1:
On the left, an extrudate of a composition containing 25% of lanreotide through a needle of 1.00 mm inner diameter
In the middle an extrudate of a composition at 19% of lanreotide through a needle of 1.00 mm inner diameter
On the right, an extrudate of a composition containing 19% of lanreotide through a needle of 0.60 mm inner diameter The results obtained with a needle with an inner diameter of 1.00 mm gave similar extrudates. It has not been possible to make the same comparison with a 0.60 mm needle: only the composition at 19% of lanreotide can be extruded manually and the extrudate is significantly different.

EXAMPLE 11

Manual Injection

For doses of compositions prepared according to Example 2 at 19% lanreotide pre-filled in standard 1.00 mL glass syringes, it was possible to verify that manual injection can be carried out using a standard hypodermic needle of 21 G of 25 mm. These manual injections were performed using standard finger-rests and available for standard commercial syringes.

The tests are carried out using standard needles attached extemporaneously to the various syringes allowing normal or deep subcutaneous injections to be considered depending on the length of the needle varying from 10 to 20 mm, such as intramuscular injections with long needles of 25 to 40 mm.

The combination of the advantages of needle implantation and delivery of product with less force, choice of injection site, less viscous deposit which retains its shape less or diffuses more and reduced volume by the precipitation of lanreotide are all factors which contribute to making these treatments easier, more comfortable, less painful to administer and better tolerated at the site of deposition by avoiding sensitive nodules.

EXAMPLE 12

Stability Study of Compositions at 20% of Lanreotide in Water and in a Water-Ethanol Mixture.

A composition at 25% of lanreotide prepared as described in Example 1 with a mixture of purified water and 75:25 ethyl alcohol was tested for stability at 5° C. and 25° C./60% RH. After 1 month of storage under these conditions, the purity of the peptide determined by RP-HPLC is compared to the initial purity. The results are reported in the following table.

| Purity at t = 0 | Purity at t = 1 month and storage at 5° C. | Purity at t = 1 month et storage at 25° C./60% RH |
|---|---|---|
| 99.1% Ar | 99.1% Ar | 98.9% Ar |

The stability of different compositions was studied according to protocols making it possible to predict the feasibility of ready-to-use presentations under different manufacturing conditions, aseptically or with terminal sterilization. Compositions of 20% lanreotide have been shown to be stable.

Unexpectedly when considering other data with a low percentage of organic solvent, it was found that compositions with a water mixture containing 10% or less ethanol were also stable.

It is therefore possible with these 2 types of less viscous sustained and/or controlled release compositions to provide a ready-to-use injectable product presentation without steps of reconstitution of the product before injection.

EXAMPLE 13

Pharmacokinetic (PK) Profiles Obtained in Rats

In order to verify the functioning and the feasibility of new injectable products based on these new presentations, pharmacokinetic studies on rats and on dogs were carried out.

The following 2 compositions prepared according to Example 1 starting with lanreotide acetate were tested on the rat:
Formulation A: 24.6% of lanreotide in a mixture of purified water and ethyl alcohol at 75:25

Formulation B: 27.9% of lanreotide in purified water.

Doses around 15 mg are injected subcutaneously and blood samples taken throughout the study. The various plasma samples derived from the blood samples are analyzed by LC-MS to determine the plasma concentration of lanreotide.

Figure 2:
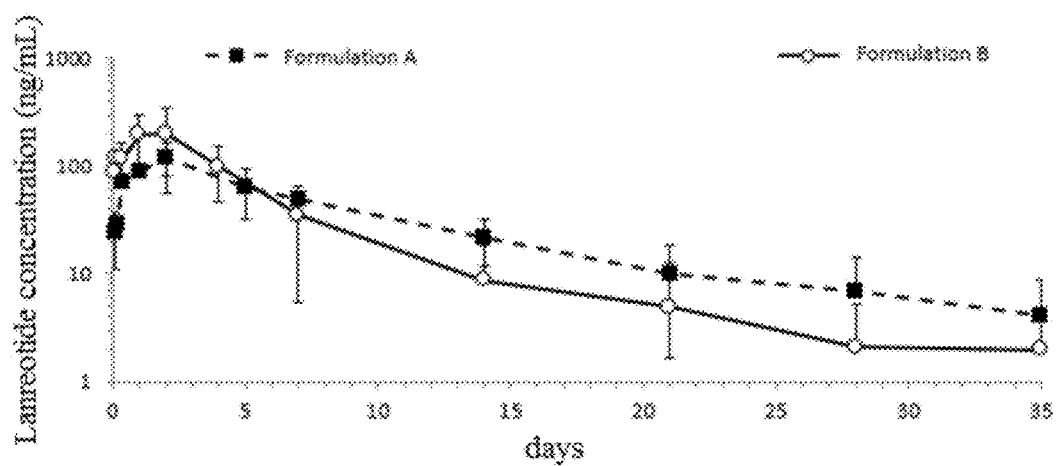
FIG. 2 shows the change in the plasma concentration of lanreotide as a function of time for the two compositions A and B prepared according to Example 13

The results are visible in FIG. 2, on which is plotted the evolution of the plasma concentration of lanreotide as a function of time for the two compositions A and B. In both cases, a prolonged release of lanreotide is observed. However, it is clearly visible that composition A, although containing a lower percentage of lanreotide gives an improvement in the release profile: the initial burst or Cmax is reduced, which makes it possible to almost double the levels of lanreotide at 4 weeks.

It is possible to test this new presentation with for example a needle of 1.00 mm in diameter and a composition containing 20% of lanreotide and compare it with the known references of a commercial composition at 25% injected with a needle of 1, 20 mm in diameter.

The results obtained in this example suggest that it is then possible to obtain comparable or even better controlled release profiles with a new presentation according to the invention thanks to the arrangement of the deposit in its mode of precipitation. It is then possible to estimate that this type of new presentation with the appropriate needles can, for example, in the case of acromegaly, allow subcutaneous administrations every 28 days with a release profile presenting less burst and a level higher at the end of the interval; or again, for example, intramuscular administrations every 14 days with a release profile at all points higher followed by a rapid drop in the levels of lanreotide for treating neuroendocrine tumors.

In order to verify the functioning of the new controlled forms, it is also possible to test this new presentation under extreme conditions of much lower viscosity, for example from a preparation containing 20% of lanreotide in a water-alcohol mixture at 95:5%. In this case, it is possible to show that we keep control of the release towards these limits and that it is also possible to thus have new more advantageous profiles, such as for example the possibility of obtaining release levels, higher, better adapted and necessary for certain treatments as in the case of NETs.

EXAMPLE 14

Example of Pharmacokinetic Profile (PK) Obtained in Dogs

In general, presentations according to the invention are capable of giving profiles with higher doses administered to dogs than to rats, thus easier to compare with the doses used in humans in the clinic.

A batch prepared according to Example 1 from lanreotide acetate in purified water is tested in dogs and at a concentration of 20.2% of lanreotide. Doses of 60 mg (lanreotide) are injected intramuscularly and blood samples are taken throughout the study. The doses are packaged in syringes of 3.0 mm in diameter coupled to needles of 0.8×0.6×19 mm. The intramuscular administration with these small diameter needles is carried out without problem.

The various plasma samples derived from the blood samples are analyzed by LC-MS to determine the plasma concentration of lanreotide.

Figure 3:
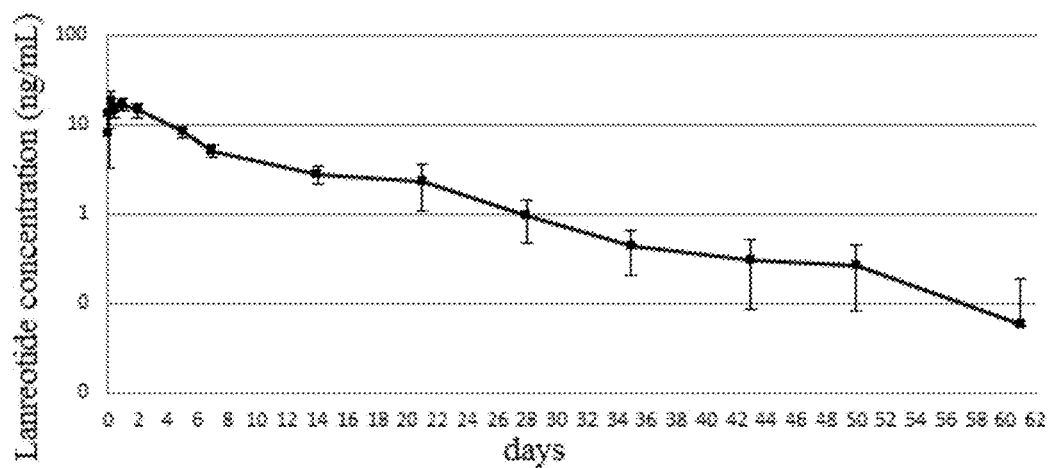
FIG. 3 shows the change in the plasma concentration of lanreotide as a function of time for the composition prepared according to Example 14

A prolonged release of lanreotide is observed over a period of at least 1 month. The results are visible in FIG. 3, on which the evolution of the plasma concentration of lanreotide is plotted as a function of time.

EXAMPLE 15

Pharmacokinetic Profile (PK) Obtained in Dogs

A formulation prepared according to Example 1 from lanreotide acetate and a 93:7% mixture of purified water/ethyl alcohol is tested on the dog at a lanreotide concentration of 20.7%. Doses of 60 mg of lanreotide are injected intramuscularly and blood samples taken throughout the study. The various plasma samples derived from the blood samples are analyzed by LC-MS to determine the plasma concentration of lanreotide.

Figure 4:
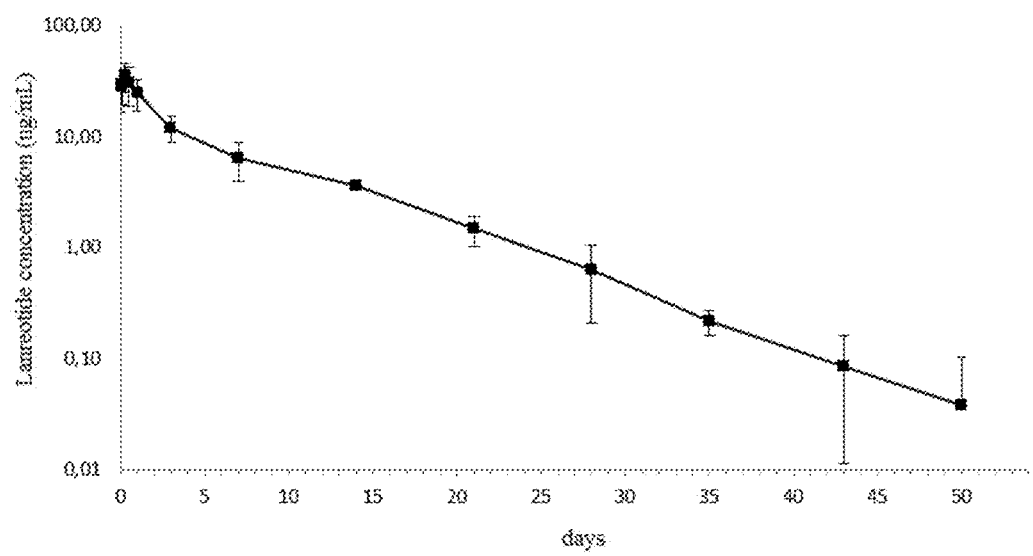
FIG. 4 shows the change in the plasma concentration of lanreotide as a function of time for the composition prepared according to Example 15

The results are visible in FIG. 4, on which the evolution of the plasma concentration of lanreotide is plotted as a function of time.

A prolonged release of lanreotide is observed for a period of at least 1 month.

EXAMPLE 16

Preparation of an Aqueous Composition of Lanreotide with Arginine and Analytical Results of Purity A new composition is obtained from 0.40 g of lanreotide acetate and a solution of L-arginine, at 0.072 g/g in purified water. The composition is obtained by mixing lanreotide acetate with 2.67 g of solution of arginine. The 2 components are weighed in 5 mL plastic syringes.

The mixing is carried out by back and forth movement between the 2 syringes connected by a connector as described in Example 1. At the end of the mixing phase, the composition is distributed into plastic syringes of 1.0 ml (around 530 mg of composition per syringe). This composition can be injected as such is or can be lyophilized to obtain a form ready to be reconstituted before injection. RP-HPLC analyzes carried out on the products as described in Example 5 indicate the purity of the peptide is maintained above 95% (98.6%).

EXAMPLE 17

Pharmacokinetic Profile (PK) Obtained in the Rat with a Composition Containing Arginine A solid composition of lanreotide acetate with L-arginine is tested on the rat. The composition is prepared from an aqueous composition containing 11% of lanreotide to ultimately obtain a lanreotide content of 57.9% w/w with approximately 0.57 g of arginine per g of lanreotide.

Doses of approximately 3.5 mg are injected subcutaneously and blood samples taken throughout the study. The various plasma samples derived from the blood samples are analyzed by LC-MS to determine the plasma concentration of lanreotide.

Figure 5:
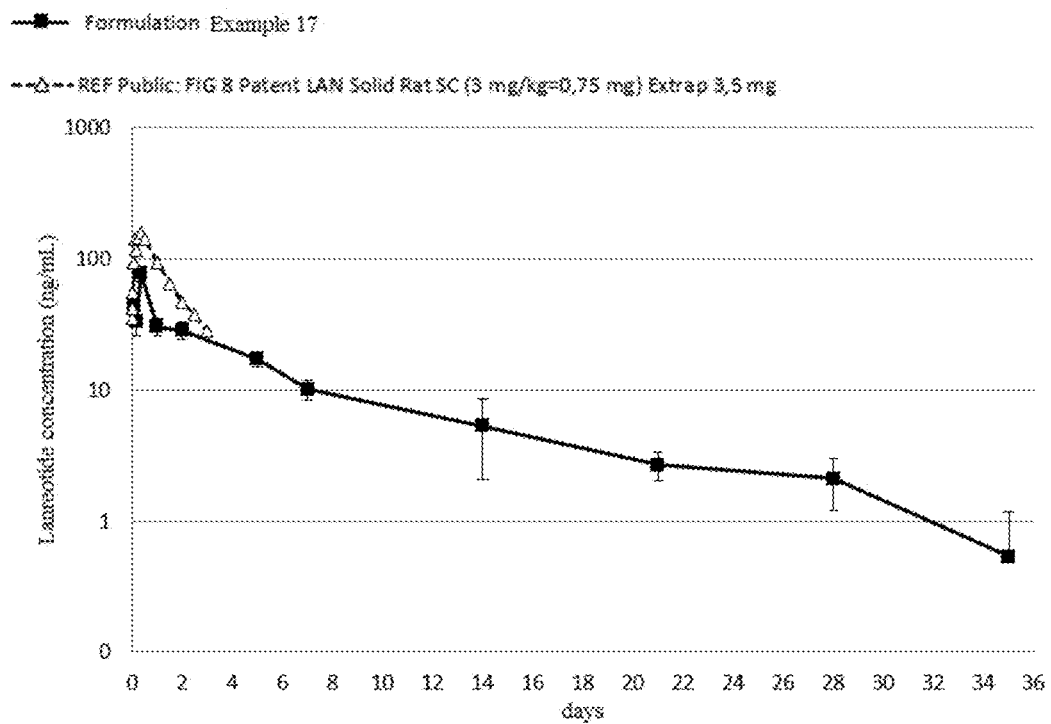
FIG. 5 represents the change in the plasma concentration of lanreotide as a function of time for the composition prepared according to Example 17

The results are visible in FIG. 5, on which the evolution of the plasma concentration of lanreotide is plotted as a function of time. A prolonged release of lanreotide is observed for a period of at least 4 weeks. By comparison, an improvement in the profile is obtained compared to the PK profile of the equivalent forms without arginine.

EXAMPLE 18

Determination of the Form of Deposits by Palpation and by Extemporaneous Sampling of Different Compositions Injected Subcutaneously in Rabbits, Results and Possible Extrapolations Solutions at different concentrations are prepared as described in Example 1.

Formulation A: formulation containing 20% of lanreotide in water

Formulation B: formulation containing 20% of lanreotide in a water/ethanol mixture 95:5%

Reference Formulation: formulation containing 25% of lanreotide in water which reproduces the conditions of current commercial products.

These formulations are injected into the rabbit according to the following model:

A first arm is injected at t=0 with 30 mg of Formulation A and 30 mg of Reference Formulation at two different injection sites; at t=7 days with 30 mg of Formulation A at a third injection site, and at t=11 days with 30 mg of Formulation A at a fourth injection site, i.e. 4 injections in total;

A second arm is injected at t=0 with 30 mg of Formulation B and 30 mg of Reference Formulation at two different injection sites; at t=7 days with 30 mg of Formulation B at a third injection site, and at t=11 days with 30 mg of Formulation B at a fourth injection site, i.e. 4 injections in total;

It is possible to perceive the various deposits through the skin by the touch in order to follow the evolution of their shape and their consistency, and after two weeks to verify their nature by taking an extemporaneous sample.

It is noted that for these same low doses of 30 mg of lanreotide injected, the deposits prepared from Reference Formulation, however smaller in volume, are more sensitive or palpable than those of Formulations A or B. The less viscous deposits produced from the water-mixture. Alcohol of Formulation B are the least palpable.

After 2 weeks at the time of sacrifice of the animals, it is noted that all the deposits at 20% of Formulation A or Formulation B after 3, 7 or 14 days show a more or less solid white mass which corresponds to the precipitation of lanreotide. The lanreotide content of these deposits is analyzed, and it is found that the remaining amounts of this peptide were inversely proportional to the time after injection and comparable at 2 weeks with those obtained with the deposit of the Reference Formulation.

This demonstrates the possibility of obtaining with these new presentations which combine finer needles and more diluted compositions, controlled compositions of lanreotide over a week and more according to a different release process.

The invention claimed is:

1. A pre-filled syringe wherein:
a) its diameter is greater than 3.00 mm, and it is equipped with a standard needle having an outer diameter equal to or less than 1.00 mm and an inner diameter equal to or less than 0.80 mm and a length between 10 and 40 mm,
b) it contains a pharmaceutical composition comprising:
1) an aqueous solvent consisting of water and optionally of an organic solvent miscible with water,
2) lanreotide or one of its salts, at a concentration ranging from 11 to 25% by weight of lanreotide relative to the total weight of the composition,
3) optionally one or more amino acids,
4) optionally a monomeric excipient accepted by the pharmacopoeia.

2. The pre-filled syringe according to claim 1, wherein the composition is configured for parenteral administration by subcutaneous, normal or deep, or intramuscular injection into a patient of said composition using said syringe releases lanreotide or lanreotide salt over a period of at least 7 days, 7 to 14 days, 14 to 28 days.

3. The pre-filled syringe according to claim 1, wherein the composition further comprises ethanol in a proportion of between 3% and 23% by weight relative to the total weight of the composition.

4. The pre-filled syringe according to claim 1, wherein the one amino acid is arginine, at a concentration ranging from 0.1 to 13% by weight relative to the total weight of the composition.

5. The pre-filled syringe according to claim 1, wherein the syringe is a manual syringe with piston rod provided with a standard needle of the luer-lock type having an outer diameter of 0.80 to 1.00 mm, an inner diameter of 0.60 to 0.80 mm and a length of 20 to 30 mm.

6. The manual syringe according to claim 5 with a piston rod fitted with a standard needle of the luer-lock type having an outer diameter of 0.80 to 1.00 mm, an inner diameter and 0.60 to 0.80 mm and a length of about 20 mm, pre-filled with a sustained-release pharmaceutical composition for parenteral administration, said composition comprising an aqueous solvent consisting of water and optionally 3% ethyl alcohol, acetate of lanreotide in an amount sufficient so that the lanreotide concentration is approximately 18% to 21% or 22% or even 25% by weight relative to the total weight of the composition, and optionally arginine at a concentration ranging from 0.1 to 13% by weight relative to the total weight of the composition.

7. The manual syringe according to claim 5 with a piston rod provided with a standard needle of the luer-lock type having an outer diameter of 0.80 mm, an inner diameter of 0.60 mm and a length of 20 mm, pre-filled with a sustained release pharmaceutical composition for parenteral administration, said composition comprising water and lanreotide acetate in sufficient quantity such that the lanreotide concentration is about 20% by weight relative to water.

8. The pre-filled syringe according to claim 2, wherein the one amino acid is arginine, at a concentration ranging from 0.1 to 13% by weight relative to the total weight of the composition.

9. The pre-filled syringe according to claim 3, wherein the one amino acid is arginine, at a concentration ranging from 0.1 to 13% by weight relative to the total weight of the composition.

10. The pre-filled syringe according to claim 2, wherein the syringe is a manual syringe with piston rod provided with a standard needle of the luer-lock type having an outer diameter of 0.80 to 1.00 mm, an inner diameter of 0.60 to 0.80 mm and a length of 20 to 30 mm.

11. The pre-filled syringe according to claim 3, wherein the syringe is a manual syringe with piston rod provided with a standard needle of the luer-lock type having an outer diameter of 0.80 to 1.00 mm, an inner diameter of 0.60 to 0.80 mm and a length of 20 to 30 mm.

12. The pre-filled syringe according to claim 8, wherein the syringe is a manual syringe with piston rod provided with a standard needle of the luer-lock type having an outer diameter of 0.80 to 1.00 mm, an inner diameter of 0.60 to 0.80 mm and a length of 20 to 30 mm.

13. The pre-filled syringe according to claim 9, wherein the syringe is a manual syringe with piston rod provided with a standard needle of the luer-lock type having an outer diameter of 0.80 to 1.00 mm, an inner diameter of 0.60 to 0.80 mm and a length of 20 to 30 mm.

14. The manual syringe according to claim 2 with a piston rod fitted with a standard needle of the luer-lock type having an outer diameter of 0.80 to 1.00 mm, an inner diameter and 0.60 to 0.80 mm and a length of about 20 mm, pre-filled with a sustained-release pharmaceutical composition for parenteral administration, said composition comprising an aqueous solvent consisting of water and optionally 3% ethyl alcohol, acetate of lanreotide in an amount sufficient so that the lanreotide concentration is approximately 18% to 21% or 22% or even 25% by weight relative to the total weight of the composition, and optionally arginine at a concentration ranging from 0.1 to 13% by weight relative to the total weight of the composition.

15. The manual syringe according to claim 3 with a piston rod fitted with a standard needle of the luer-lock type having an outer diameter of 0.80 to 1.00 mm, an inner diameter and 0.60 to 0.80 mm and a length of about 20 mm, pre-filled with a sustained-release pharmaceutical composition for parenteral administration, said composition comprising an aqueous solvent consisting of water and optionally 3% ethyl alcohol, acetate of lanreotide in an amount sufficient so that the lanreotide concentration is approximately 18% to 21% or 22% or even 25% by weight relative to the total weight of the composition, and optionally arginine at a concentration ranging from 0.1 to 13% by weight relative to the total weight of the composition.

16. The pre-filled syringe according to claim 1, wherein the aqueous solvent comprises ethanol.

\* \* \* \* \*